United States Patent [19]

Jenck

[11] Patent Number: 4,522,760
[45] Date of Patent: Jun. 11, 1985

[54] RECOVERY OF PALLADIUM VALUES FROM CARBONYLATION REACTION MEDIUM

[75] Inventor: Jean Jenck, Villeurbanne, France

[73] Assignee: Rhone-Poulenc Chimie de Base, Courbevoie, France

[21] Appl. No.: 401,394

[22] Filed: Jul. 23, 1982

[30] Foreign Application Priority Data

Sep. 16, 1981 [FR] France .................. 81 17463

[51] Int. Cl.$^3$ .............................................. C11C 3/02
[52] U.S. Cl. ........................... 260/410.9 R; 260/410; 260/410.5; 260/410.7; 556/136; 260/413; 560/233; 560/248
[58] Field of Search ............ 260/410, 410.9 R, 410.5, 260/410.7, 413 R, 429 R; 560/233, 248

[56] References Cited

U.S. PATENT DOCUMENTS

| | | | |
|---|---|---|---|
| 4,013,583 | 3/1977 | Knifton | 260/429 R X |
| 4,013,584 | 3/1977 | Knifton | 260/429 R X |
| 4,034,004 | 7/1977 | Cassar et al. | 260/413 R |
| 4,042,530 | 8/1977 | Knifton | 260/429 R X |
| 4,124,617 | 11/1978 | Knifton | 260/410.6 X |
| 4,172,087 | 10/1979 | Knifton | 260/410.6 |
| 4,268,689 | 5/1981 | Knifton | 260/410.6 X |
| 4,269,781 | 5/1981 | Wanderspurt et al. | 260/410.9 R |

*Primary Examiner*—Helen M. S. Sneed
*Attorney, Agent, or Firm*—Burns, Doane, Swecker & Mathis

[57] ABSTRACT

Palladium values are separated from the products of reaction resulting from the carbonylation of a conjugated diene with carbon monoxide in the presence of an alcohol, a halogenated hydracid and a palladium catalyst, by (i) contacting the carbonylation reaction medium with a nitrogen, phosphorus or arsenic quaternary onium salt, a polar alcohol and an apolar, aliphatic or cycloaliphatic hydrocarbon solvent, and permitting the resulting admixture to phase separate into an alcohol phase and an organic phase; (ii) decanting/separating said alcohol phase from said organic phase; (iii) recovering the palladium values and the quaternary onium salt from said alcohol phase; and (iv) recovering the products of carbonylation from said organic phase.

23 Claims, No Drawings

RECOVERY OF PALLADIUM VALUES FROM CARBONYLATION REACTION MEDIUM

BACKGROUND OF THE INVENTION

1. Field of the Invention

The present invention relates to the separation of the palladium from the reaction medium resulting from the carbonylation of conjugated dienes with CO, in the presence of an alcohol, a halogenated hydracid and a palladium catalyst.

A principal advantage of the present invention resides in the fact that the palladium is separated in alcoholic solution and can be directly recycled for additional carbonylation catalysis, while at the same time retaining its activity.

2. Description of the Prior Art

It is known to this art, from Japanese Pat. No. 48.5564, to prepare monoesters of $\beta,\gamma$-unsaturated carboxylic acids by the carbonylation of conjugated dienes with carbon monoxide, in the presence of a monoalcohol, a non-halogenated palladium catalyst and a halogenated hydracid, at a temperature on the order of 100° C. and under a carbon monoxide pressure on the order of 100 bars; the patent is silent regarding any method for recycling the palladium catalyst.

And U.S. Pat. No. 4,172,087 describes the synthesis of pent-3-enoic acid esters mixed with a large amount of nona-3,8-dienoic acid esters, by the carbonylation of butadiene with carbon monoxide, in the presence of an alcohol, a heterocyclic tertiary amine and a palladium halide complexed with a monodentate tertiary phosphine or a non-halogenated palladium salt complexed with a polydentate tertiary phosphine; the presence of a monodentate tertiary phosphine and a heterocyclic tertiary amine enables recovery of a liquid containing the palladium catalyst, after distillation of the pent-3-enoic acid esters and the nona-3,8-dienoic acid esters; the said liquid can be recycled into the medium to be carbonylated. A process of this type is carried out in the absence of halogenated hydracid; it displays a very low selectivity in respect of pent-3-enoic acid esters.

SUMMARY OF THE INVENTION

Accordingly, a major object of the present invention is the provision of an improved process for the separation of the palladium from the reaction product resulting from the carbonylation of conjugated dienes with carbon monoxide, in the presence of an alcohol, a halogenated hydracid and a palladium catalyst, the focus of the carbonylation reaction being to synthesize esters of $\beta,\gamma$-unsaturated carboxylic acids, and said process comprising:

(i) contacting the carbonylation reaction medium with a quaternary onium salt of an element of Group VB of the Periodic Table selected from among nitrogen, phosphorus and arsenic, a polar alcohol and an apolar, aliphatic or cycloaliphatic hydrocarbon solvent, and permitting the resulting admixture to phase separate into an alcohol phase and an organic phase;

(ii) decanting and separating said alcohol phase and said organic phase;

(iii) recovering the palladium and the quaternary onium salt from said alcohol phase; and (iv) recovering the products of carbonylation from said organic phase.

DETAILED DESCRIPTION OF THE INVENTION

By "alcohol phase" as utilized herein, there is intended the phase in which the solvent consists of the alcohol present during the contacting operation.

By "organic phase" as utilized herein, there is intended the phase in which the solvent consists of the apolar hydrocarbon solvent present during the contacting operation.

Exemplary of the quaternary onium salts which are used according to the invention, representative are those possessing any anion and a quaternary onium cation having one of the following four structural formulae:

(I)

(II)

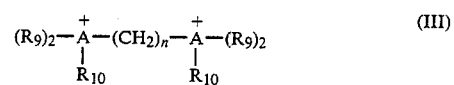

(III)

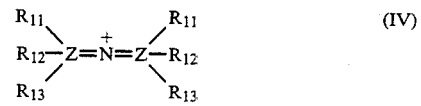

(IV)

in which:

A represents nitrogen, phosphorus or arsenic;

$R_1$, $R_2$, $R_3$ and $R_4$ are identical or different and represent:

a linear or branched chain alkyl radical having from 1 to 16 carbon atoms, the said alkyl radical being optionally substituted by a phenyl, hydroxyl, halogeno, nitro, alkoxy or alkoxycarbonyl group;

a linear or branched chain alkenyl radical having from 2 to 12 carbon atoms, preferably from 4 to 8 carbon atoms, and very particularly an alkenyl radical derived from the conjugated diene employed in the reaction; or an aryl radical having from 6 to 10 carbon atoms, the said aryl radical being optionally substituted by at least one alkyl group containing from 1 to 4 carbon atoms, or at least one alkoxy, alkoxycarbonyl or halogeno group;

it also being possible for two of the said radicals $R_1$ to $R_4$ to together form a linear or branched chain alkylene, alkenylene or alkadienylene radical having from 3 to 6 carbon atoms;

$R_5$, $R_6$, $R_7$ and $R_8$ are identical or different and represent:

a linear or branched chain alkyl radical having from 1 to 4 carbon atoms;

it being possible for the radicals $R_7$ and $R_8$ to together form an alkylene radical having from 3 to 6 carbon atoms and for the radicals $R_6$ and $R_7$ or $R_6$ and $R_8$ to together form an alkylene, alkenylene or alkadienylene radical having 4 carbon atoms and forming a nitrogen-containing heterocyclic ring with the nitrogen atom;

$R_9$ represents a linear or branched chain alkyl radical having from 1 to 4 carbon atoms or a phenyl radical;

$R_{10}$ represents:
a linear or branched chain alkyl radical having from 1 to 4 carbon atoms, which is identical to or different from $R_9$; or
a linear or branched chain alkenyl radical having from 2 to 12 carbon atoms, preferably from 4 to 8 carbon atoms, and very particularly an alkenyl radical derived from the conjugated diene to be carbonylated;

n represents an integer which is greater than or equal to 1 and less than or equal to 10 and preferably less than or equal to 6;

Z represents phosphorus or arsenic; and $R_{11}$, $R_{12}$ and $R_{13}$ are identical or different and represent:
a linear or branched chain alkyl radical having from 1 to 16 carbon atoms; or
an aryl radical having from 6 to 10 carbon atoms.

The following cations are exemplary of quaternary onium cations corresponding to the formula I: tetramethylammonium, triethylmethylammonium, tributylmethylammonium, trimethyl(n-propyl)-ammonium, tetraethylammonium, tetrabutylammonium, tetrapropylammonium, tetrapentylammonium, tetrahexylammonium, tetraheptylammonium, tetraoctylammonium, tetradecylammonium, dodecyltrimethylammonium, methyltrioctylammonium, tetradodecylammonium, tetraoctadecylammonium, hexadecyltrimethylammonium, butyltripropylammonium, methyltributylammonium, pentyltributylammonium, heptyltributylammonium, methyldiethylpropylammonium, ethyldimethylpropylammonium, benzyltributylammonium, benzyltriethylammonium, phenyltrimethylammonium, benzyltrimethylammonium, benzyldimethylpropylammonium, benzyldimethyloctylammonium, benzyldimethyltetradecylammonium, benzyldimethylhexadecylammonium, dimethyldiphenylammonium, methyltriphenylammonium, but-2-enyltriethylammonium, N,N-dimethyl-tetra-methyleneammonium, N,N-diethyl-tetramethylammonium, tetramethylphosphonium, tetrabutylphosphonium, ethyltrimethylphosphonium, trimethylpentylphosphonium, octyltrimethylphosphonium, dodecyltrimethylphosphonium, trimethylphenylphosphonium, diethyldimethylphosphonium, dicyclohexyldimethylphosphonium, dimethyldiphenylphosphonium, cyclohexyltrimethylphosphonium, triethylmethylphosphonium, methyl-tri-(isopropyl)-phosphonium, methyl-tri-(n-propyl)-phosphonium, methyl-tri-(n-butyl)-phosphonium, methyl-tri-(2-methylpropyl)-phosphonium, methyltricyclohexylphosphonium, methyltriphenylphosphonium, methyltribenzylphosphonium, methyl-tri-(4-methylphenyl)-phosphonium, methyltrixylylphosphonium, Diethylmethylphenylphosphonium, dibenzylmethylphenylphosphonium, ethyltriphenylphosphonium, tetraethylphosphonium, ethyl-tri-(n-propyl)-phosphonium, triethylpentylphosphonium, hexadecyltributylphosphonium, ethyltriphenylphosphonium, n-butyl-tri-(n-propyl)-phosphonium, butyltriphenylphosphonium, benzyltriphenylphosphonium, ($\beta$-phenylethyl)-dimethylphenylphosphonium, tetraphenylphosphonium, triphenyl-(4-methylphenyl)-phosphonium, tetrakis-(hydroxymethyl)-phosphonium, tetrakis-(2-hydroxyethyl)-phosphonium and tetraphenylarsonium.

The following cations are exemplary of the cations corresponding to the formula II: N-methylpyridinium, N-ethylpyridinium, N-hexadecylpyridinium and N-methylpicolinium.

The following cations are exemplary of the cations corresponding to the formula III: 1,3-bis-(but-2-enyldimethylammonium)-propane, 1,2,-bis-(trimethylammonium)-ethane, 1,3-bis-(trimethylammonium)-propane, 1,4-bis-(trimethylammonium)-butane and 1,3-bis-(trimethylammonium)-butane.

The following cation is exemplary of a cation corresponding to the formula IV: bis-(triphenylphosphino)-iminium.

The following ions are representative of anions of the said quaternary onium salts: $F^-$, $ClO_4^-$, $PF_6^-$, $BF_4^-$, $B\Phi_4^-$, $PO_4^{3-}$, $HPO_4^{2-}$, $H_2PO_4^-$, $CH_3SO_3^-$,

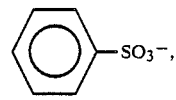

$HSO_4^-$, $NO_3^-$, $SO_4^{2-}$, $Cl^-$, $Br^-$, $I^-$, $SCN^-$, $CN^-$ and $RS^-$, in which R represents an optionally substituted $C_1$-$C_6$ alkyl radical or $C_6$-$C_{10}$ aryl radical.

For reasons of convenience of use, the said anions are advantageously selected from among: $PO_4^{3-}$, $HPO_4^{2-}$, $H_2PO_4^-$, $CH_3SO_3^-$,

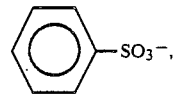

$NO_3^-$, $SO_4^{2-}$, $PF_6^-$, $Cl^-$ and $Br^-$, and preferably $Cl^-$.

Among the alcohols which can be present for conducting the contacting operation, representative are linear or branched chain aliphatic monoalcohols containing from 1 to 4 carbon atoms and preferably from 1 to 3 carbon atoms, employed either alone or in any admixture thereof; the alcohol present during the said operation can advantageously be the same as that used to carry out the carbonylation reaction, this because of the larger or smaller amount of unconverted alcohol generally present in the medium resulting from the carbonylation reaction.

The apolar hydrocarbon solvents required for the contacting operation have a dielectric constant $\epsilon$ of less than 2.3 (value measured at 20°-25° C.) and preferably of less than 2.1.

The following are exemplary of such solvents: pentane ($\epsilon = 1.84$), isopentane ($\epsilon = 1.84$), hexane ($\epsilon = 1.89$), cyclohexane ($\epsilon = 2.02$), octane ($\epsilon = 1.95$), cyclooctane ($\epsilon = 1.95$), 2,2,4-trimethylpentane (isooctane, $\epsilon = 1.94$), decane ($\epsilon = 1.99$), dodecane ($\epsilon = 2.01$), tetradecane, hexadecane or their mixtures of the petroleum ether type.

The term "contacting reagents" will hereafter be used to denote the quaternary onium salt, the alcohol and the apolar hydrocarbon solvent which are present during the contacting step according to the invention.

The amounts of the said contacting reagents are selected such as to provide a good separation of the two phases after decantation, and to achieve the desired degree of separation of the palladium, and to do this in an economically advantageous manner.

The degree of separation of the alcohol phase from the organic phase is the greater:

(a) the higher the molar ratio onium cation/palladium;

(b) the higher the weight ratio quaternary onium salt/alcohol; and (c) the greater the difference between the dielectric constant of the alcohol and that of the apolar hydrocarbon solvent.

It is obvious that it is not economically advantageous to use too large an excess of the quaternary onium salt or to use excessive amounts of alcohol and solvent.

To carry out the subject process satisfactorily, the following amounts are advantageously present during the contacting operation:

(1) an amount of quaternary onium salt corresponding to a molar ratio quaternary onium cation/palladium of at least about 10 and preferably ranging from 20 to 200; and (2) amounts of alcohol and apolar hydrocarbon solvent which are at least equal to those required for the decantation of the contacting medium to provide an alcohol phase and an organic phase.

In general, the following amounts are representative:

(3) an amount of alcohol corresponding to a weight ratio quaternary onium salt/alcohol of at least about 0.1 and preferably ranging from 0.25 to 30; and (4) an amount of solvent corresponding to a weight ratio solvent/alcohol of more than about 1 and preferably of more than about 1.5.

An improvement to the process according to the present invention, which improvement permits a better separation of the alcohol phase containing the palladium catalyst, comprises subjecting the alcohol phase obtained after decantation to one or more extraction and separation operations with the aid of the apolar hydrocarbon solvent.

The contacting step is carried out under temperature conditions which make it possible to obtain a good separation of the two phases, and to do this in an economically advantageous manner. The relative miscibility of an alcohol with an alkane generally decreases with decreasing temperature; it has been found that the solubility of the quaternary onium salt in the alcohol also decreases, but that it nevertheless remains high; thus, the contacting step can be carried out at low temperature and preferably at a temperature close to ambient temperature.

The present invention also relates to the various embodiments of the process for the separation of the palladium from the products resulting from the carbonylation of conjugated dienes with carbon monoxide, in the presence of an alcohol, a halogenated hydracid and a palladium catalyst.

A first embodiment of said process is characterized in that:

(i) the medium resulting from the carbonylation reaction, which may contain unconverted alcohol, is treated with a quaternary onium salt in an amount defined above, an apolar hydrocarbon solvent and, if appropriate, alcohol, the amounts of solvent and alcohol being adjusted such as to achieve a separation of the alcohol phase and the organic phase after decantation; and (ii) the alcohol phase containing the alcohol, the quaternary onium salt and the palladium catalyst is recovered.

A second embodiment of said process is characterized in that:

(i) the quaternary onium salt is selected from among those in which the anion is "hard" or "intermediate" base [according to the conventional definition set forth by R. Pearson in *J. Chem. Ed.*, 45, 581-7 (1968)];

(ii) the said quaternary onium salt is used in whole or in part during the carbonylation reaction;

(iii) the medium resulting from the carbonylation reaction, which contains the onium salt and may contain unreacted alcohol, is treated with onium salt, if necessary, such as to satisfy the onium/Pd molar ratio defined above, an apolar hydrocarbon solvent and, if appropriate, alcohol, the amounts of solvent and alcohol being adjusted such as to achieve separation of the alcohol phase and the organic phase after decantation; and (iv) the alcohol phase containing the alcohol, the quaternary onium salt and the palladium catalyst is recovered, this alcohol phase optionally being recycled into the carbonylation reaction.

The following ions are exemplary of the "hard" or "intermediate" bases which can constitute the anion of the said onium salts: $F^-$, $ClO_4^-$, $PF_6^-$, $BF_4^-$, $B\Phi_4^-$, $PO_4^{3-}$, $HPO_4^{2-}$, $CH_3SO_3^-$,

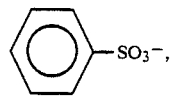

$HSO_4^-$, $NO_3^-$, $SO_4^{2-}$, $Cl^-$, $Br^-$ and $H_2PO_4^-$.

For reasons of convenience of use, the said anions are advantageously selected from among: $PO_4^{3-}$, $HPO_4^{2-}$, $H_2PO_4^-$, $CH_3SO_3^-$,

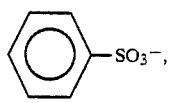

$NO_3^-$, $SO_4^{2-}$, $PF_6^-$, $Cl^-$ and $Br^-$, and preferably $Cl^-$.

This second embodiment is very particularly advantageous in view of the fact that the alcohol phase containing the quaternary onium salt and the palladium catalyst, which phase is recovered after decantation, can be directly recycled into the medium subjected to carbonylation, without significant modification of the performance characteristics of the catalyst.

In fact, it has been found (the subject of French patent application No. 81/01,205, filed Jan. 23, 1981, and assigned to the assignee hereof) that conjugated dienes can be carbonylated in the presence of alcohol, halogenated hydracid, a palladium catalyst and a quaternary onium salt possessing a "hard" or "intermediate" anion; a beneficial effect, in particular on the degree of conversion of the dienes and the selectivity of the process in respect of the desired esters of $\beta,\gamma$-unsaturated carboxylic acids, has been found in the case where the amount of onium salt used corresponds to a molar ratio onium cation/palladium of at least about 0.5, in particular if the said onium cation corresponds to one of the formulae I to IV above.

A particularly advantageous effect has been found for a molar ratio onium cation/palladium ranging from 1 to 15.

As the presence of the onium salt in a much larger amount, corresponding to that required for the subsequent separation of the palladium, has absolutely no adverse effect on the carbonylation reaction, the advantage of this second embodiment, with the possibility of recycling the alcohol phase containing the palladium catalyst and the onium salt, is immediately apparent.

A variant of the aforesaid two embodiments comprises using all or a portion of the apolar organic solvent during the carbonylation reaction.

An improvement to said two embodiments comprises subjecting the alcohol phase which has been separated off to a complementary treatment which comprises subjecting the said alcohol phase to one or more extraction and separation operations with the aid of the said apolar hydrocarbon solvent.

The process of the invention is very particularly suitable for the separation of the palladium from products resulting from the carbonylation of conjugated dienes having the buta-1,3-diene skeleton in their molecule, and from linear or branched chain aliphatic monoalcohols containing from 1 to 4 carbon atoms, in the presence of hydrochloric acid and a palladium catalyst, at a temperature ranging from 50° to 150° C. and under a CO pressure preferably ranging from 50 to 250 bars.

The following are representative of the conjugated dienes having the buta-1,3-diene skeleton in their molecule:

(1) linear or branched chain aliphatic dienes containing from 4 to 12 carbon atoms and preferably from 4 to 8 carbon atoms, which are optionally substituted by inert groups such as: phenyl, cyclohexyl, nitro, oxo and, in particular, alkoxycarbonyl; and (2) cyclic dienes containing from 6 to 8 carbon atoms.

Specific examples of conjugated dienes which are representative are buta-1,3-diene, isoprene, piperylene, hexa-1,3-diene, hexa-2,4-diene, chloroprene, 1-cyclohexylbuta1,3-diene, 1-phenylbuta-1,3-diene, octa-2,4-diene, 3-methylpenta-1,3-diene, 2-methylpenta-2,4-diene, cyclohexa-1,3-diene, cycloocta-1,3-diene and the like, which are optionally substituted by an alkoxycarbonyl group, such as methyl penta-2,4-dienoate.

The alcohol which can be used to carry out the carbonylation and contacting operations is a monoalcohol containing from 1 to 4 carbon atoms and preferably from 1 to 3 carbon atoms, if the carbonylation reaction is carried out in the presence of a quaternary onium salt comprising a "hard" or "intermediate" anion; the said alcohol can contain from 2 to 4 carbon atoms and preferably 2 or 3 carbon atoms if the carbonylation reaction is carried out in the absence of quaternary onium salt.

The carbonylation is advantageously carried out in the presence of hydrochloric acid, which can be introduced into the carbonylation medium in the gaseous form or in the form of an organic compound capable of releasing HCl in the medium, for example, in the form of 1-chlorobut-2-ene or 3-chlorobut-1-ene in the case of the carbonylation of butadiene.

The following are exemplary of the palladium catalysts present during the carbonylation reaction:

(1) palladium metal deposited on a support, such as charcoal, alumina, silica or the like;

(2) palladium oxides;

(3) salts or complexes of palladium II in which the anion coordinated to the Pd cation is a "hard" or "intermediate" base, in particular the salts or the $\pi$-allyl complexes of Pd in which the anion coordinated to the Pd cation is selected from among the following anions: carboxylates, such as formate, acetate, propionate and benzoate; $SO_4^{2-}$; $NO_3^-$; acetylacetonate; and halides, such as $Cl^-$ and $Br^-$, and preferably $Cl^-$; or (4) complexes of palladium zero comprising organic ligands not containing elements of group VB, representative of such complexes being bis-(dibenzalacetone)-Pd or bis-(cycloocta-1,5-diene)-Pd.

The amounts of reagents to be used in order to carry out the carbonylation reaction can vary over very wide limits; it is obvious that said amounts will be selected such that the process is economically advantageous.

Thus, although it is possible to use from 0.5 to 10 times the amount of alcohol required by stoichiometry, it is preferable, in order to attain maximum conversion of the conjugated diene while at the same time avoiding excessive dilution of the medium with alcohol, to carry out the process with a molar ratio alcohol/conjugated diene ranging from about 0.8 to 5 and preferably on the order of 1.

Likewise, the good activity of the palladium catalyst makes it possible to use the said catalysts in very small amounts (corresponding to a molar ratio conjugated diene/palladium on the order of 2,500); the use of a larger amount of catalyst (corresponding to molar ratio conjugated diene/palladium on the order of 100) is not disadvantageous; as the desired object is to carry out a sufficiently rapid and selective carbonylation without consuming too much catalyst, a ratio conjugated diene/palladium ranging from about 100 to 2,000 is generally preferable.

The amount of halogenated hydracid to be used corresponds to a molar ratio halogenated hydracid/palladium of more than about 2. However, in order to avoid any risk of degradation of the alcohol to form alkyl chlorides and dialkyl ethers (this degradation being due to a excessive concentration of hydracid in the medium), a molar ratio halogenated hydracid/palladium ranging from 2 to 150 and preferably ranging from 5 to 100 will advantageously be selected.

The individual entities corresponding to the term "mols" are as follows:

(1) Alcohol: gram molecule
(2) Conjugated diene: gram molecule
(3) Halogenated hydracid: gram molecule
(4) Palladium: gram atom
(5) Quaternary onium cation: gram ion In order to further illustrate the present invention and the advantages thereof, the following specific examples are given, it being understood that same are intended only as illustrative and in nowise limitative.

The abbreviations indicated in the tables which follow corresponding to the noted examples have the following meanings:

Ex: example;
BD: butadiene;
ROH: alcohol;
Me: methyl; Et: ethyl; Met: 2-methoxyethyl; Bu: n-butyl;
$\Omega$: phenyl; Pd(DBA)$_2$ bis-(dibenzalacetone)-Pd; [<(Pd-Cl]2 bis-($\pi$-allyl-chloropalladium);
catalyst: palladium catalyst;
co-catalyst: HCl or reaction product of HCl+conjugated diene employed;
onium: quaternary onium salt;
alkane: apolar hydrocarbon solvent;
RM: reaction mass resulting from the carbonylation (containing the unconverted butadiene together with volatile products which evaporate during the subsequent contacting operation carried out at ambient temperature);

$P_3$: pent-3-enoic acid ester;
$P_4$: pent-4-enoic acid ester;
$P_2$: pent-2-enoic acid ester;
$P'$: 2-methylbut-3-enoic acid ester;
$C_9$: nona-3,8-dienoic acid ester;
$C_6$: $C_6$ dialkyl esters (mostly dialkyl 2-methylglutarate);
$HC_8$: butadiene dimers (essentially 4-vinylcyclohexene);
PA: pentanoic acid ester and 2-methylbutanoic acid ester;
$ROC_4$: 3-alkoxybut-1-ene and 1-alkoxybut-2-ene;
$ClC_4$: 3-chlorobut-1-ene and 2-chlorobut-2-ene;
ClPA: chloropentanoic acid ester;
Cl:
  alkyl chloride
  dialkyl ether
  (side reaction of HCl with the alcohol)
DC: overall degree of conversion of the butadiene (in mol %);
RY: partial degree of conversion (in mol %) for each product obtained, relative to the butadiene introduced, with $DC = \Sigma_i RY_i$.

In the calculation of DC, only the RY of the following products are taken into account: $P_3$, $P_4$, $P_2$, $P'$, $C_9$, $C_6$, $HC_8$, PA, $ROC_4$ and ClPA; in effect, the chlorobutenes ($ClC_4$) are equivalent to a mixture of butadiene + HCl, which can be carbonylated to $P_3$.

S: selectivity (in mol %) for each product, with S = RY/DC;
RYCl: partial degree of conversion (in mol %) to ethyl chloride and diethyl ether, relative to the ethanol introduced;
A: specific activity of the catalyst, expressed as the number of mols of $P_3$ and $P_4$ obtained per g atom of Pd and per hour;
CO: technical-grade CO gas containing about 0.8% by volume of hydrogen, which does not have an appreciable effect on the carbonylation reaction.

EXAMPLE 1

First carbonylation step

The following materials were introduced, under a stream of argon, into a 125 cm$^3$ autoclave made of nickel-molybdenum alloy marketed under the trademark HASTELLOY B2:
(i) 0.075 g (namely, 0.423 millimol) of anhydrous palladium (II) chloride;
(ii) 30.8 g (namely, 513 millimols) of propan-2-ol; and
(iii) 3.82 g (namely, 42.25 millimols) of 1-chlorobut-2-ene, which corresponds to a molar ratio of HCl/Pd of 100.

The autoclave was closed; 13 g (namely, 240.7 millimols) of butadiene were transferred therein, which corresponds to a molar ratio butadiene/Pd of 569 and a molar ratio alcohol/butadiene of 2.13.

The autoclave, which was agitated by shaking, was heated to 120° C. and charged with technical-grade CO gas containing about 0.8% by volume of hydrogen, at a constant total pressure of 145 bars. The reaction was permitted to proceed for 2 hours at this temperature. The autoclave was then cooled to 15° C. and slowly degassed.

46.67 g of a yellow homogeneous solution, containing 43.6% by weight of isopropanol and 42.3% by weight of isopropyl pentenoates, were recovered.

Table I reports the results of gas chromatographic analysis of the solution obtained, together with the S and RY corresponding to each product formed.

The overall degree of conversion of the butadiene, DC, was 61.9 mol %.

The specific activity A of the catalyst was 166 hour$^{-1}$.

Contacting, decantation and separation steps.

First experiment:

1.21 g of the yellow solution obtained as above, containing 1.17 mg (namely, 0.011 millimol) of Pd, were taken and 6.40 g of n-octane were added thereto; the solution remained homogeneous.

0.21 g of $PBu_4^+Cl^-$ was then added thereto and the composition thus obtained contained:
(1) 6.7% by weight of isopropanol;
(2) 6.7% by weight of pentenoic acid esters;
(3) 2.7% by weight of $PBu_4^+Cl^-$, which corresponds to a molar ratio $PBu_4^+/Pd$ of 65 and a weight ratio of $PBu_4^-Cl^-/isopropanol$ of 0.40; and
(4) 81.1% by weight of octane, which corresponds to a weight ratio octane/alcohol of 12.

The medium separated into two phases:
(a) a colorless upper phase (7.03 g) containing
  (i) the octane and:
  (ii) about 90% of the isopropyl pent-3-enoate present at the start of the contacting operation;
  (iii) about 100% of the isopropyl nona-3,8-dienoate and of the $C_6$ diesters; and
  (iv) less than 2 ppm of palladium; and
(b) a viscous yellow lower phase (0.79 g) containing the residual isopropanol, the phosphonium salt and more than 99% of the palladium catalyst treated.

Second carbonylation step

The aforesaid alcohol phase was used in a further carbonylation step using identical charges of reactants and under the same conditions as in the first carbonylation step; the isopropyl pent-3-enoate produced corresponds to a specific activity of about 210 hour$^-$.

Second experiment:

A contacting step was carried out in the same manner on 1.37 g of the yellow solution resulting from the carbonylation operation and containing 1.32 mg (namely, 0.012 millimol) of palladium, with the aid of 2.24 g of octane and 0.55 g of $PBu_4^+Cl^-$.

The composition thus obtained contained:
(1) 14.4% by weight of isopropanol;
(2) 14% by weight of pentenoic acid esters;
(3) 13.2% by weight of $PBu_4^+Cl^-$, which corresponds to a molar ratio $PBu_4^+Cl^-/Pd$ of 150 and a weight ratio $PBu_4^+Cl^-/isopropanol$ of 0.92;
(4) 53.8% by weight of octane, which corresponds to a weight ratio octane/alcohol of 3.7.

The mixture separated into two phases:
(a) a colorless upper phase (2.94 g) containing:
  (i) about 85% of the isopropyl pent-3-enoate present at the start of the contacting operation;
  (ii) about 100% of the isopropyl nona-3,8-dienoate and of the $C_6$ diester; and
  (iii) less than 3 ppm of palladium; and
(b) a viscous yellow lower phase (1.21 g) containing the residual isopropanol, the phosphonium salt and more than 99% of the palladium catalyst treated.

EXAMPLE 2

Carbonylation step.

A carbonylation reaction was carried out under conditions similar to those of Example 1, in the presence of:
(1) ethanol as the alcohol; and
(2) gaseous HCl as the co-catalyst.
The amounts of reactants used were as follows:
(i) 10 g (namely, 185.2 millimols) of butadiene;
(ii) 36.8 g (namely, 800 millimols) of absolute ethanol;
(iii) 60.3 mg (namely, 0.34 millimol) of $PdCl_2$,
(iv) 248.2 mg (namely, 6.8 millimols) of gaseous HCl, which corresponds to the following molar ratios: HCL/Pd=20, ethanol/butadiene=4.3 and butadiene/Pd=545.

The carbonylation reaction was carried out for 2 hours at 120° C. and a constant total pressure of 145 bars, carbon monoxide being continuously charged.

After carbonylation, 45.9 g of a very light yellow, homogeneous solution were recovered. Table II reports the results of gas chromatographic analysis of the solution obtained, together with the S and RY corresponding to each product formed.

The overall degree of conversion DC of the butadiene was 24.3 mol %.

The specific activity A of the catalyst was 47 hour$^-$.

Contacting, decantation and separation steps 5.68 g of n-decane were added to a sample of 2.83 g of reaction mass containing 2.18 g of ethanol, which corresponds to a weight ratio alkane/alcohol of 2.6; the mixture remained homogeneous. Separation into two phases was effected by adding 0.60 g of tetra-(hydroxymethyl)phosphonium chloride, which corresponds to a weight ratio $P(CH_2OH)_4^+Cl^-$/alcohol of 0.27 and a molar ratio onium/Pd of 150.

The colorless upper phase (8.03 g) consisted essentially of n-decane and contained less than 5 ppm of Pd.

The lower phase (1.05 g), which had an intense green coloration, contained the residual ethanol and virtually the entire amount of the phosphonium salt and of the palladium catalyst.

EXAMPLE 3

The carbonylation reaction described in Example 2 was carried out under similar conditions, for 2 hours, at 120° C. and under a constant total pressure of 145 bars, CO being continuously charged. The amounts of reactants used were as follows:
(i) butadiene 23 g (namely, 426 millimols)
(ii) absolute ethanol 66.2 g (namely, 1,440 millimols)
(iii) $PdCl_2$ 150 g (namely, 0.845 millimol)
(iv) gaseous HCl 1.54 g (namely, 42.2 millimols)
The molar ratios were:

$$\frac{HCl}{Pd} = 50 \qquad \frac{BD}{Pd} = 504$$

After carbonylation, 88.8 g of reaction mass, which was a light yellow homogeneous solution, were recovered. Table III reports the results of the chromatographic analysis and the values of S and RY.

The degree of conversion of the butadiene, DC, was 53.9% and the activity A of the catalyst was 121 hour$^{-1}$.

The composition by weight of the reaction mass was 30% of $P_3$ and 62% of ethanol. 50 g of n-octane were added thereto and the reaction mass was subjected to distillation, which extracted 66.5 g of a mixture containing 20.3 g of octane and 41.2 g of ethanol. 9 g of $PBu_4^+Cl^-$ were added to the non-volatile phase; the composition was then as follows:
(1) 14.1 g of ethanol,
(2) 28.8 g of octane,
(3) 9.0 g of $PBu_4^+Cl^-$,
namely, a weight ratio alkane/alcohol of 2.04, a weight ratio onium/alcohol of 0.64 and a molar ratio onium/Pd of 36.

There was a separation into two phases:
(a) a colorless upper organic phase weighing 55.7 g and containing 3.5 ppm of Pd; and
(b) a green-yellow lower alcohol phase weighing 23.5 g.

EXAMPLES 4 TO 8

Carbonylation step

Carbonylation reactions were carried out under conditions similar to those of Example 1:
(1) in the presence of ethanol as the alcohol, instead of isopropanol, and also
(2) in the presence of an apolar hydrocarbon solvent selected from among n-octane, n-tetradecane and n-pentane.

The said carbonylations were carried out at 120° C. for 2 hours at a constant total pressure of 120 bars, CO being continuously charged.

The amounts of reactants used and the results of the carbonylations are reported in Tables IV A and IV B.

Contacting, decantation and separation steps

Various samples of the solutions obtained using the different apolar solvents were subjected to contacting operations with the aid of the various onium salts shown in Table IV C.

This table also indicates:
(1) the composition of the sample treated;
(2) the amounts of onium salt used;
(3) the minimum amount of onium salt beyond which phase separation was observed ("minimum onium");
(4) the color and the composition of the upper organic phase; and
(5) the color and the composition of the lower alcohol phase.

Example 4 was repeated, $NBu_4^+BF_4^-$ being replaced by $P\Phi_4^{+Cl-}$, $NBu_4^+CH_3SO_3^-$ or $\Phi_3P=N=P\Phi_3^+Cl^-$; in the same manner, separation into two phases was observed giving a colorless upper organic phase and a lower alcohol phase of the following color:
(a) straw yellow in the presence of $P\Phi_4^+Cl^-$,
(b) very pale yellow in the presence of $NBu_4^{+CH_3SO_3^-}$,
(c) bright yellow in the presence of $\Phi_3P=N=P\Phi_3^+Cl^-$.

EXAMPLE 9

(9 a) Carbonylation step

A carbonylation reaction was carried out under conditions similar to those of Example 1, in the presence of the amounts of reactants shown in Table VA.

The said operation was carried out for 3 hours at 100° C. and under a constant total pressure of 100 bars, CO continuously charged.

The results of the said operation are reported in Table VB..

(9 b) Contacting, decantation and separation steps

The reaction mass obtained was then treated with 70 g of n-octane.

The medium separated into two phases (the weights of which are given in Table VC):

(a) a colorless upper phase, the composition of which is reported in Table VD and which contained at most 4 ppm of Pd;

(b) a yellow-green lower phase containing the ethanol and at least 99.3% of the Pd.

(9 c) Recycling

The alcohol phase, which contained about 0.421 mg atom of Pd, was recycled into the carbonylation autoclave.

Ethanol, 1-chlorobut-2-ene and butadiene were also introduced into the said autoclave, in amounts corresponding to the molar ratios indicated in step (9 a).

The carbonylation reaction was carried out for 3 hours at 100° C. and at a constant total pressure of 100 bars, CO continuously charged therein.

The results of the carbonylation operation are reported in Table VB.

EXAMPLES 10–23

The carbonylation reaction described in Example 1 was carried out in the presence of:

(1) various alcohols selected from among: methanol (MeOH), ethanol (EtOH) and 2-methoxyethanol (MetOH);
(2) various palladium catalysts: $PdCl_2$, bis(dibenzalacetone)-Pd and bis-($\pi$-allyl-chloropalladium);
(3) gaseous HCl or chlorobutenes; and also
(4) various quaternary onium salts possessing a "hard" or "intermediate" anion.

The nature and the amounts of reactants and the conditions of temperature and CO pressure used are reported in Tables VA and VIA.

The results of the carbonylation reactions are reported in Tables VB and VIB.

The solutions obtained, or samples of solutions, were then treated with an apolar alkane in the amounts indicated in Tables VC and VIC.

The analysis of the alcohol phases and organic phases obtained after decantation is reported in Table VD.

The alcohol phases separated off were then optionally subjected to one or more complementary extraction-separation treatments with the aid of an apolar alkane in the amounts indicated in Tables VC and VIC. Table VD reports the analysis of the various successive organic phases, where appropriate.

The petroleum ether used in Example 17 was a distillation cut having a boiling point of between 40° and 65° C. and consisting of alkanes essentially containing 5 carbon atoms.

Experiments 19′ and 19″

The reaction medium resulting from the carbonylation operation described in Example 19 was subjected to a contacting operation with the aid of solvents having a dielectric constant of more than 2.3, instead of apolar solvents. No separation could be observed using one of the following apolar solvents for 5 g of reaction mass:

| toluene (from 0 to 7.55 g) | $\epsilon = 2.38$ |
|---|---|
| chloroform (from 0 to 11.8 g) | $\epsilon = 4.81$ |

EXAMPLE 24

A carbonylation reaction similar to that of Example 12 was carried out, the medium to be carbonylated also containing octane.

The amounts of reactants were as follows:

(i) 269 millimols of butadiene;
(ii) 261 millimols of ethanol;
(iii) 0.423 millimol of $PdCl_2$ (molar ratio butadiene/Pd=635);
(iv) 8.45 millimols of 1-chlorobut-2-ene (molar ratio HCl/Pd =20);
(v) 42.3 millimols of $PBu_4^+Cl^-$ (molar ratio onium/Pd=100); and
(vi) 14 g of octane.

The reaction was carried out for 2 hours at 120° C. and under a constant total pressure of 120 bars.

56.52 g of a yellow solution, containing 3.30 g of ethanol and 14 g of octane, were recovered.

The results of gas chromatographic analysis are reported in Table VIB, together with the RY and S for each product.

The overall degree of conversion of the butatdiene, DC, was 62.7% and the activity of the catalyst, A, was 181 hour$^{-1}$.

The solution was then treated with 100 cm$^3$ of octane. The following materials were thus present:

(1) 45 mg of palladium;
(2) 3.3 g of ethanol;
(3) 84 g of octane;
(4) 12.46 g of $PBu_4^{+Cl-}$, which corresponds to a molar ratio $PBu_4^+Cl^-$/Pd of about 100, a weight ratio $PBu_4^+Cl^-$/ethanol of 3.8 and a weight ratio octane/ethanol of 25.4.

The following were recovered after decantation:

(a) 23.6 g of a yellow-orange alcohol phase; and
(b) 98.4 g of a colorless organic phase containing less than 2.5 ppm of palladium.

EXAMPLE 25

A carbonylation reaction was carried out using the following amounts of reactants:

(i) methyl penta-2,4-dienoate: 4.825 g (namely, 43 millimols)
(ii) methanol: 1.4 g (namely, 43.8 millimols)
(iii) 1-chlorobut-2-ene: 385 mg (namely, 4.25 millimols);
(iv) $PdCl_2$: 15 mg (namely, 0.085 millimol); and
(v) $PBu_4^+Cl^-$ 2.51 g (namely, 8.5 millimols).

The reaction was carried out for 2 hours at 90° C. and under a pressure of 145 bars. 9.06 g of a fairly viscous, lemon-yellow homogeneous solution were recovered.

The results of gas chromatographic analysis performed upon the resultant solution were as follows:

2.15 g of carbonylation products (unsaturated $C_6$ diesters) consisting of:

37.7% of 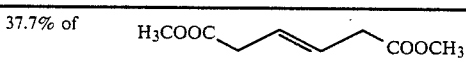

| | |
|---|---|
| 41.9% of | H₃COOC-CH(CH₃)-CH=CH-COOCH₃ |
| 14.4% of | CH₂=CH-CH(COOCH₃)-CH₂-COOCH₃ |
| 6.0% of | H₃COOC-CH=CH-CH(CH₃)-COOCH₃ | and 1.62 g of methyl penta-2,4-dienoate dimers.

The specific activity, over all the unsaturated $C_6$ diesters, was 74 hour$^{-1}$.

4.60 g of the reaction mass were taken and treated with 17 g of octane. The composition was then as follows:

(1) 0.46 g of methanol;
(2) 4.57 mg of Pd;
(3) 1.27 g of PBu₄Cl; and
(4) 17 g of octane, namely, a molar ratio onium/Pd of 100, a weight ratio onium/alcohol of 2.76 and a weight ratio alkane/alcohol of 37.

There was separation into two phases:

(a) a colorless upper phase weighing 18.7 g and containing 26% of the unsaturated $C_6$ diesters, 63% of the $C_{10}$ diesters ("dimers"), 45% of the unreacted substrate, less than 1 ppm of palladium and less than 5 ppm of phosphorus; and (b) a viscous lemon-yellow lower phase weighing 2.80 g.

EXAMPLE 26

A carbonylation reaction was carried out using the following amounts of reactants:

(i) isoprene: 27.25 g (namely, 400 millimols);
(ii) ethanol: 18.40 g (namely, 400 millimols);
(iii) 1-chlorobut-2-ene: 2.716 g (namely, 30 millimols);
(iv) bis-($\pi$-allyl-chloro-palladium): 179.7 mg (namely, 1.0 mg atom of Pd); and
(v) PBu₄Cl: 8.85 g (namely, 30 millimols)

which corresponds to the following molar ratios:

$$\frac{\text{diene}}{\text{Pd}} = 400 \qquad \frac{\text{HCl}}{\text{Pd}} = 30$$

The reaction was carried out for 4 hours at 100° C. and under a total pressure of 200 bars. 62.1 g of a lemon-yellow homogeneous solution were recovered.

The chromatographic analysis indicated that 33.75 g of carbonylation products (unsaturated $C_6$ esters), consisting of 94% of ethyl 4-methylpent-3-enoate, were obtained.

The specific activity, calculated on the ethyl 4-methylpent-3-enoate, was 56 hour$^{-1}$.

31 g of the reaction mass were taken and treated with 50 cm³ of n-octane. The composition was then as follows:

(1) 53.2 mg of palladium;
(2) 4.42 g of PBu₄Cl;
(3) 2.92 g of ethanol; and
(4) 35 g of octane, which corresponds to a molar ratio onium/Pd of 30, a weight ratio onium/alcohol of 1.52 and a weight ratio alkane/alcohol of 12.

After separation into the two phases, the colored lower phase was twice again treated with 25 cm³ of octane. After decantation, all the colorless upper phases were combined and the following were recovered:

(a) an orange limpid homogeneous lower ethanol phase weighing 8.70 g, which contained 98.6% of Pd; and (b) a colorless limpid upper octane phase having a volume of 126 cm³ (91.6 g); the octane had therefore extracted 26 cm³ (21.6 g) of organic products (namely, 93% of the said products); this phase contained about 6 ppm of palladium.

TABLE I

| Products formed | Weight, g | Millimols | S, % | RY, % |
|---|---|---|---|---|
| isopropoxybutene, ROC₄ | 0.056 | 0.5 | 0.3 | 0.2 |
| 4-vinylcyclohexene, HC₈ | 0.141 | 2.6 | 1.7 | 1.1 |
| isopropyl 2-methylbut-3-enoate, P' | 0.375 | 2.6 | 1.72 | 1.1 |
| isopropyl pent-4-enoate, P₄ | 0.064 | 0.5 | 0.3 | 0.2 |
| isopropyl pent-3-enoate, P₃ | 19.727 | 138.9 | 93.2 | 57.7 |
| isopropyl pent-2-enoate, P₂ | 0.074 | 0.5 | 0.3 | 0.2 |
| isopropyl chloropentanoate, ClPA | 0.136 | 0.8 | 0.5 | 0.3 |
| isopropyl nona-3,8-dienoate, C₉ | 0.176 | 1.8 | 1.2 | 0.7 |
| C₆ diesters | 0.182 | 0.8 | 0.5 | 0.3 |

TABLE II

| Products formed | Weight, g | Millimols | S, % | RY, % |
|---|---|---|---|---|
| ethoxybutene, ROC₄ | 0.14 | 1.4 | 3.1 | 0.7 |
| 4-vinylcyclohexene, HC₈ | 0.12 | 2.2 | 4.9 | 1.2 |
| ethyl 2-methylbut-3-enoate, P' | 0.08 | 0.6 | 1.3 | 0.3 |
| ethyl pentenoates, P₃ + P₄ | 4.13 | 32.2 | 71.7 | 17.4 |
| ethyl nona-3,8-dienoate, C₉ | 0.46 | 8.5 | 18.9 | 4.6 |
| C₆ diesters | ε | ε | ε | ε |

TABLE III

| Products formed | Weight, g | Millimols | S, % | RY, % |
|---|---|---|---|---|
| ethoxybutene, ROC₄ | 0.40 | 4.0 | 1.8 | 0.9 |
| 4-vinylcyclohexene, HC₈ | 0.297 | 5.5 | 2.4 | 1.3 |
| ethyl 2-methylbut-3-enoate, P' | 0.845 | 6.6 | 2.9 | 1.6 |
| ethyl pentenoates, P₃ + P₄ | 26.26 | 205.1 | 90.0 | 48.5 |
| ethyl chloropentanoate, ClPA | 0.131 | 0.8 | 0.3 | 0.1 |
| ethyl nona-3,8-dienoate, C₉ | 0.255 | 2.8 | 1.2 | 0.7 |
| C₆ diesters | 0.485 | 2.4 | 1.0 | 0.6 |

TABLE IV A

| Ex | BD millimols | EtOH millimols | Catalyst millimols PdCl₂ | Co-catalyst millimols | | BD/Pd | HCl/Pd | Alkane | RM weight g | appearance |
|---|---|---|---|---|---|---|---|---|---|---|
| 4 | 259 | 261 | 0.18 | CH₂=CH-CH₂-CH₂-Cl | 9 | 1,440 | 50 | octane: 20 g | 41.0 | light yellow |
| 5 | 259 | 261 | 0.423 | HCl | 8.45 | 614 | 20 | octane: 20 g | 49.0 | lemon- |

TABLE IV A-continued

| Ex | BD milli-mols | EtOH milli-mols | Catalyst milli-mols PdCl$_2$ | Co-catalyst | millimols | BD/Pd | HCl/Pd | Alkane | RM weight g | appearance |
|---|---|---|---|---|---|---|---|---|---|---|
| 6 | 259 | 261 | 0.423 | HCl | 21.1 | 614 | 50 | octane: 20 g | 50.7 | yellow yellow-orange |
| 7 | 259 | 261 | 0.18 | ⌇⌇Cl | 9 | 1,440 | 50 | octane: 20 g | 41.0 | light yellow |
| 8 | 268 | 261 | 0.423 | ⌇⌇Cl | 2.11 | 636 | 5 | tetradecane: 20 g | 46.5 | yellow |

TABLE IV B

| Ex | DC (%) | A(hour$^{-1}$) | P$_3$ + P$_4$ S, % | RY, % | P' S, % | RY, % | C$_9$ S, % | RY, % | HC$_8$ S, % | RY, % | ROC$_4$ S, % | RY, % | RYCl | Residual ROH |
|---|---|---|---|---|---|---|---|---|---|---|---|---|---|---|
| 4 | 14.0 | 84 | 83.7 | 11.7 | 1.4 | 0.2 | 3.3 | 0.5 | 9.1 | 1.3 | 2.5 | 0.3 | 1.4 | 10.3 g |
| 5 | 71.2 | 206 | 94.5 | 67.3 | 1.8 | 1.3 | 1.7 | 1.2 | 1.6 | 1.2 | 0.4 | 0.3 | 0.3 | 3.9 g |
| 6 | 71.8 | 210 | 95.4 | 68.5 | 2.2 | 1.9 | 0.5 | 0.4 | 1.2 | 0.8 | 0.7 | 0.5 | 1.2 | 5.0 g |
| 7 | 14.0 | 84 | 83.7 | 11.7 | 1.4 | 0.2 | 3.3 | 0.5 | 9.1 | 1.3 | 2.5 | 0.3 | 1.4 | 10.3 g |
| 8 | 32.2 | 80 | 77.6 | 25.1 | 1.5 | 0.5 | 14.1 | 4.6 | 6.0 | 1.9 | 0.8 | 0.3 | | 10.2 g |

TABLE IV C

| | EXAMPLES | | | | |
|---|---|---|---|---|---|
| | 4 | 5 | 6 | 7 | 8 |
| Sample to be treated | | | | | |
| weight (g) | 41.0 | 49.0 | 50.7 | 41.0 | 46.5 |
| including: ethanol (g) | 10.3 | 3.9 | 5.0 | 10.3 | 10.2 |
| P$_3$ (g) | 3.9 | 22.3 | 22.7 | 3.9 | 8.6 |
| alkane (g) | octane:20 | octane:20 | octane:20 | octane:20 | tetradecane:20 |
| ratio: alkane/ethanol (by weight) | 1.9 | 5.1 | 4.0 | 1.9 | 2.0 |
| Contacting operation | | | | | |
| onium salt | NBu$_4^+$BF$_4^-$ | NBu$_4^+$Br$^-$ | PBu$_4^+$Cl$^-$ | NBu$_4^+$SCN$^-$ | PBu$_4^+$Cl$^-$ |
| weight of onium (g) | 2.62 | 2.75 | 5.37 | 5.17 | 4.75 |
| onium/alcohol (by weight) | 0.25 | 0.62 | 1.07 | 0.50 | 0.47 |
| onium/Pd (in mols) | 44 | 20 | 43 | 96 | 38 |
| minimum onium (g) | 0.41 | 1.15 | 1.72 | 3.28 | 2.14 |
| Alcohol phase | | | | | |
| color | orange | red | orange | bright red | orange |
| weight (g) | 17.2 | 16.5 | 27.6 | 20.6 | 19.9 |
| Organic phase | | | | | |
| color | yellowish | yellowish | colorless | yellowish | colorless |
| weight (g) | 26.4 | 35.0 | 28.2 | 25.2 | 30.4 |
| P$_3$ (g) | 6.1 | 18.7 | 14.3 | 3.2 | |
| Pd | 53 ppm | 9 ppm | 47 ppm | 2 ppm | 22 ppm |

TABLE V A

| EX | BD mmpls | ROH mmols | Catalyst milli-mols PdCl$_2$ | Catalyst millimoles | BD/PD | HCl/Pd | Onium millimoles | Onium Pd | T °C. | Duration hours | PCO bars | RM weight g | color |
|---|---|---|---|---|---|---|---|---|---|---|---|---|---|
| 9a | 269 | EtOH 261 | 0.423 | ⌇⌇Cl 21.1 | 635 | 50 | PBu$^+$Cl$^-$ 42.3 | 100 | 100 | 3 | 145 | 39.71 | light green |
| 10 | 269 | MeOH 250 | 0.423 | ⌇⌇Cl 42.2 | 592 | 100 | PBu$^+$Cl$^-$ 42.3 | 100 | 80 | 2 | 120 | 26.65 | green |
| 11 | 269 | EtOH 261 | 0.423 | ⌇⌇Cl 21.1 | 635 | 50 | PBu$^+$Cl$^-$ 42.3 | 100 | 120 | 2 | 145 | 43.51 | green |
| 12 | 250 | EtOH 261 | 0.845 | ⌇⌇Cl 8.45 | 296 | 10 | PBu$^+$Cl$^-$ 42.3 | 50 | 120 | 2 | 120 | 42 | green |

TABLE V A-continued

| EX | BD mmpls | ROH mmols | Catalyst millimols PdCl$_2$ | Catalyst millimoles | BD/PD | HCl/Pd | Onium millimoles | Onium Pd | T °C | Duration hours | PCO bars | RM weight g | RM color |
|---|---|---|---|---|---|---|---|---|---|---|---|---|---|
| 13 | 296 | MetOH 261 | 0.423 | 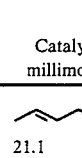 21.1 | 700 | 50 | PBu$^+$Cl$^-$ 42.3 | 100 | 120 | 2 | 145 | 42.79 | light green |
| 14 | 222 | EtOH 261 | 0.845 |  21.1 | 263 | 50 | PBu$^+$Cl$^-$ 42.3 | 50 | 120 | 4 | 145 | 44.85 | dark green |
| 15 | 259 | MeOH 250 | 1.27 |  42.2 | 205 | 33 | PBu$^+$Cl$^-$ 42.3 | 33 | 90 | 2 | 120 | 33 | light green |
| 16 | 222 | EtOH 261 | 0.423 |  21.1 | 526 | 50 | NBu$_4^+$H$_2$PO$_4^-$ 16.9 | 40 | 120 | 2 | 90 | 31.3 | light yellow |
| 17 | 232 | EtOH 261 | 0.306 |  36.85 | 756 | 120 | NBu$_4^+$CH$_3$SO$_3^-$ 12.27 | 40 | 120 | 2 | 120 | 25.5 | light yellow |

TABLE VI A

| EX | BD mmols | ROH mmols | Catalyst millimols Pd(DBA)$_2$ | Co-catalyst millimols | BD/Pd | HCl/Pd | Onium millimols | Onium Pd | T °C | Duration hours | PCO bars | RM Weight g | RM Color |
|---|---|---|---|---|---|---|---|---|---|---|---|---|---|
| 19 | 250 | EtOH 261 | 0.423 | 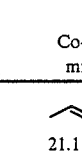 21.1 | 591 | 50 | PBu$_4^+$Cl$^-$ 42.3 | 100 | 120 | 2 | 200 | 43.1 | light green |
| 20 | 232 | EtOH 261 | 1.058 |  52.8 | 219 | 50 | PBu$_4^+$Cl$^-$ 42.3 | 40 | 120 | 1 | 145 | 41.3 | yellow-green |
| 21 | 333 | EtOH 261 | 0.423 |  21.1 | 788 | 50 | Φ$_3$P=N—PΦ$_3^+$Cl$^-$ 10.6 | 25 | 140 | 1 | 145 | 43.2 | yellow-green |
| 22 | 204 | EtOH 261 | 0.423 |  21.1 | 482 | 50 | PBu$_4^+$Cl$^-$ 42.3 | 100 | 120 | 2 | 145 | 40.72 | green |
| 23 | 241 | EtOH 261 | 0.423 |  21.1 | 569 | 50 | PΦ$_4^+$Cl$^-$ 35.1 | 83 | 120 | 2 | 145 | 37.7 | orange |
| 18 | 269 | EtOH 261 | [<(—PdCl]$_2$ 0.211 |  2.11 | 635 | 5 | PBu$_4^+$Cl$^-$ 42.2 | 100 | 120 | 2 | 200 | 41.1 | yellow |

TABLE VB

| Ex | DC % | A h-1 | P$_3$ + P$_4$ S % | P$_3$ + P$_4$ RY % | P' S % | P' RY % | C$_9$ S % | C$_9$ RY % | HC$_8$ S % | HC$_8$ RY % | ROC$_4$ S % | ROC$_4$ RY % | C$_6$ S % | C$_6$ RY % | RYCl % | Residual ROH in g | onium/ROH |
|---|---|---|---|---|---|---|---|---|---|---|---|---|---|---|---|---|---|
| 9a | 35 | 69 | 92.6 | 32.4 | 1.7 | 0.6 | 1.7 | 0.6 | 2 | 0.7 | ε | ε | 1.1 | 0.4 | 1.7 | 7.33 | 1.70 |
| 9c | 32 | 63 | 92.3 | 29.6 | 1.6 | 0.5 | 1.8 | 0.6 | 1.9 | 0.6 | ε | ε | 1.3 | 0.4 | | | |
| 10 | 19 | 54 | 95.6 | 18.2 | 1.5 | 0.3 | 0.4 | 0.1 | 1.9 | 0.4 | ε | ε | 0.6 | 0.1 | 2 | 5.62 | 2.22 |
| 11 | 63 | 181 | 90.7 | 57.1 | 1.6 | 1.2 | 1.8 | 1.1 | 2 | 1.3 | ε | ε | 2.5 | 1.6 | 3.2 | 3.3 | 3.78 |
| 12 | 73 | 100 | 92.2 | 67.4 | 1 | 0.8 | 1.8 | 1.3 | 2 | 1.4 | ε | ε | 3.1 | 2.2 | 2.5 | 1.91 | 6.52 |
| 13 | 40 | 91 | 93 | 37.1 | 1.7 | 0.7 | 5 | 2 | ε | ε | ε | ε | 0 | 0 | 2.7 | 5.65 | 2.21 |
| 14 | 89.3 | 51 | 87.8 | 78.4 | 2.1 | 1.8 | 1.2 | 1.1 | 0.9 | 0.8 | ε | ε | 4.5 | 4 | 6 | 0.47 | 26.5 |
| 15 | 45.5 | 44 | 93.9 | 42.7 | 1.5 | 0.7 | 0.9 | 0.4 | 2.7 | 1.2 | ε | ε | 0.6 | 0.2 | ε | 5.07 | 2.46 |
| 16 | 49.4 | 111 | 85.9 | 42.4 | 1.9 | 0.9 | 7.8 | 3.8 | 2.5 | 1.2 | ε | ε | 1.6 | 0.8 | 1.1 | 8.19 | 0.70 |
| 17 | 28 | 94 | 88.7 | 24.8 | 2 | 0.6 | 1.7 | 0.5 | 4.6 | 1.3 | ε | ε | 1.1 | 0.3 | 4.5 | 7.55 | 0.76 |

TABLE VIB

| Ex | DC % | A h-1 | P₃ + P₄ S % | P₃ + P₄ RY % | P' S % | P' RY % | C₉ S % | C₉ RY % | HC₈ S % | HC₈ RY % | ROC₄ S % | ROC₄ RY % | C₆ S % | C₆ RY % | RYCl % | Residual ROH in g | Onium Residual ROH by weight |
|----|------|-------|------|------|------|------|------|------|------|------|------|------|------|------|------|------|------|
| 18 | 80.7 | 233 | 90.8 | 73.3 | 1.9 | 1.5 | 1.4 | 1.1 | 0.7 | 0.6 | ε | ε | 3.6 | 2.9 | 1.3 | 2.15 | 5.80 |
| 19 | 75 | 202 | 91.4 | 68.6 | 1.5 | 1.2 | 1.2 | 0.9 | 1 | 0.8 | — | — | 3.4 | 2.6 | 3.1 | 2.29 | 5.44 |
| 20 | 35.6 | 142 | 91.4 | 32.5 | 1.7 | 0.6 | 0.7 | 0.3 | 2.6 | 0.9 | — | — | 1.5 | 0.5 | 5.9 | 6.38 | 1.95 |
| 21 | 56.8 | 390 | 87.8 | 49.9 | 1.6 | 0.9 | 1.9 | 1.1 | 1.7 | 1 | — | — | 2.8 | 1.6 | 1.7 | 5.73 | 2.12 |
| 22 | 81.4 | 170 | 87 | 70.8 | 1.3 | 1 | 1.3 | 1 | ε | ε | — | — | 6.9 | 5.6 | 3.2 | 2.75 | 4.53 |
| 23 | 65.1 | 165 | 89.1 | 58.0 | 1.4 | 0.9 | 2.2 | 1.4 | 0.4 | 0.3 | ε | ε | 3.6 | 2.3 | 2.1 | 32.55* | 0.41 |
| 24 | 62.7 | 181 | 90.9 | 57 | 1.9 | 1.2 | 3.2 | 2 | 1.8 | 1.2 | 0.2 | 0.1 | 1.9 | 1.2 | 1.1 | 3.3 | 3.78 |

*supplementary addition of alcohol up to 32.55 g in order to solublize all of the onium salt.

TABLE V C

| Ex | Alkane added | Alkane ROH by weight | Alcohol phase* g | Organic phase No. 1 g | Complementary treatments alkane | Complementary treatments organic phases No. | Complementary treatments organic phases weight g |
|----|----|----|----|----|----|----|----|
| 9a | octane 70 g | 4.8 | 25.2 yellow-green | 79.1 colorless | — | — | — |
| 10 | octane 35 g | 6.2 | 21.1 green | 32.9 colorless | octane 35 g | No. 2 | 35.2 |
| 11 | octane 35 g | 10.6 | 16.5 green | 42.4 colorless | octane 2 × 35 g | No. 2 | 45.3 |
|    |    |    |    |    |    | No. 3 | 38.1 |
| 12 | octane 70 g | 36.6 | 16.3 green | 95.9 colorless | — | — | — |
| 13 | octane 62 g | 11.0 | 19.8 green | 81.1 colorless | — | — | — |
| 14 | iso-octane 50 g | 106 | 20.0 orange | 81.1 colorless | — | — | — |
| 15 | octane 17.5 g | 3.4 | 17.3 light brown | 20.8 colorless | octane 2 × 35 g | No. 2 | 39.4 |
|    |    |    |    |    |    | No. 3 | 39.5 |

*after all the treatments with the alkane, where appropriate.

TABLE VI C

| Ex | Alkane added | Alkane ROH by weight g | Alcohol phase g | Organic phase g |
|----|----|----|----|----|
| 16 | petroleum ether | 33 g | 3.7 | 14.6 orange | 44.9 colorless |
| 17 | octane | 35 g | 4.6 | 17.8 orange | 40.7 colorless |
| 18 | octane | 74 g | 34.6 | 20.2 yellow | 94.1 colorless |
| 19 | pentane per 5 g of RM | 6.25 g | 23.5 | 2.7 orange | 8.5 colorless |
| 19' | cyclohexane per 5 g of RM | 7.1 g | 26.7 | 2.9 orange | 9.1 colorless |
| 19" | dodecane per 5 g of RM | 7.02 g | 26.3 | 3.1 orange | 8.9 colorless |
| 20 | octane | 39 g | 6.1 | 29.1 orange | 41 yellow |
| 21 | octane | 34 g | 5.9 | 13.8 light brown | 59.3 colorless |
| 22 | octane | 35 g | 12.7 | 31.3 yellow-green | 41.2 colorless |
| 23 | decane per 10 g of RM | 36.5 g | 8.41 | 4.9 yellow | 40.7 colorless |

TABLE V D

| Ex | Organic phase No. | P₃, % | C₉, % | HC₈, % | C₆, % | Pd, ppm |
|----|----|----|----|----|----|----|
| 9a | 1 | 75 |  |  |  | ≦4 |
| 10 | 1 | 69 |  | 100 | 80 | 2.6 |
|    | 2 | 88 |  | 100 | 100 | 0.1 |
| 11 | 1 | 61 | 75 | 77 |  | 10.6 |
|    | 2 | 88 | 100 | 100 |  | 0.7 |
|    | 3 | 96 | 100 | 100 |  | <0.1 |
| 12 | 1 | 97 | 100 |  | 100 | <5 |
| 13 | 1 |  |  |  |  | <3 |
| 14 | 1 | 98 | 100 | 96 | 100 | 2.9 |
| 15 | 1 | 35 | 62 | 43 |  | 17.5 |
|    | 2* | 58 | 88 | 61 |  | 2.1 |
|    | 3 | 66 | 88 | 90 |  | 0.1 |
| 16 | 1 |  |  |  |  | 20 |
| 17 | 1 |  |  |  |  | 8 |
| 18 | 1 | 85 | 81 | 69 |  | 3.7 |
| 19 | 1 |  |  |  |  | 8 |
| 19' | 1 |  |  |  |  | 15 |
| 19" | 1 |  |  |  |  | 2 |
| 20 | 1 |  |  |  |  | 2.8 |
| 21 | 1 |  |  |  |  | 0.5 |
| 22 | 1 |  |  |  |  | 5 |
| 23 | 1 |  |  |  |  | <0.2 |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A process for the separation of palladium values from the products of reaction resulting from the alkoxycarbonylation of a conjugated diene with carbon monoxide in the presence of an alcohol, hydrochloric acid or a compound capable of releasing hydrochloric acid and a palladium catalyst to prepare esters of $\beta,\gamma$-unsaturated carboxylic acid, comprising (i) contacting the carbonylation reaction medium with a nitrogen, phosphorus or arsenic quaternary onium salt, a polar alcohol and an apolar, aliphatic or cycloaliphatic hydrocarbon solvent, and permitting the resulting admixture to phase separate into an alcohol phase and an organic phase; (ii) decanting/separating said alcohol phase from said organic phase; (iii) recovering the palladium values and the quaternary onium salt from said alcohol phase; and (iv) recovering the products of carbonylation from said organic phase.

2. The process as defined by claim 1, wherein the quaternary onium salt comprises a cation having one of the following structural formulae I to IV:

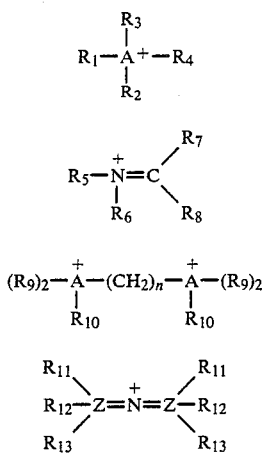

in which:

A represents nitrogen, phosphorus or arsenic;

$R_1$, $R_2$, $R_3$ and $R_4$ are identical or different and each represents:

a linear or branched chain alkyl radical having from 1 to 16 carbon atoms, or a phenyl, hydroxyl, halogeno, nitro, alkoxy or alkoxycarbonyl substituted such radical;

a linear or branched chain alkenyl radical having from 2 to 12 carbon atoms; or an aryl radical having from 6 to 10 carbon atoms, or said aryl radical substituted by at least one alkyl group having from 1 to 4 carbon atoms, or at least one alkoxy, alkoxycarbonyl or halogeno group, with the proviso that two of said radicals $R_1$ to $R_4$ may together form a linear or branched chain alkylene, alkenylene or alkadienylene radical having from 3 to 6 carbon atoms;

$R_5$, $R_6$, $R_7$ and $R_8$ are identical or different and each represents:

a linear or branched chain alkyl radical containing from 1 to 4 carbon atoms, with the proviso that the radicals $R_7$ and $R_8$ may together form an alkylene radical having from 3 to 6 carbon atoms and the radicals $R_6$ and $R_7$ or $R_6$ and $R_8$ may together form an alkylene, alkenylene or alkadienylene radical containing 4 carbon atoms and forming a nitrogen-containing heterocyclic ring with the nitrogen atom;

$R_9$ represents a linear or branched chain alkyl radical having from 1 to 4 carbon atoms or a phenyl radical;

$R_{10}$ represents:

a linear or branched chain alkyl radical having from 1 to 4 carbon atoms, and which is identical or different from $R_9$; or a linear or branched chain alkenyl radical having from 2 to 12 carbon atoms;

n represents an integer which is greater than or equal to 1 and less than or equal to 10;

Z represents phosphorus or arsenic; and $R_{11}$, $R_{12}$ and $R_{13}$ are identical or different and each represents:

a linear or branched chain alkyl radical having from 1 to 16 carbon atoms; or an aryl radical having from 6 to 10 carbon atoms.

3. The process as defined by claim 2, wherein $R_1$, $R_2$, $R_3$, $R_4$ and $R_{10}$ are alkenyl radicals having form 4 to 8 carbon atoms.

4. The process as defined by claim 3, wherein $R_1$, $R_2$, $R_3$, $R_4$ and $R_{10}$ are alkenyl radicals derived from the reactant conjugated diene.

5. The process as defined by any of claims 2 to 4, wherein n is an integer which is less than or equal to 6.

6. The process as defined by claim 2, wherein said quaternary onium salt cation is one of the following cations: tetramethylammonium, tetraethylammonium, tetrabutylammonium, tetradodecylammonium, methyltrioctylammonium, hexadecyltrimethylammonium, methyltriphenylammonium, benzyltrimethylammonium, but-2-enyltriethylammonium, tetramethylphosphonium, tetrabutylphosphonium, hexadecyltributylphosphonium, ethyltrimethylphosphonium, methyltriphenylphosphonium, hexadecylpyridinium, 1,3-bis-(but-2-enyldimethylammonium)propane, tetraphenylarsonium, tetrakis-(hydroxymethyl)phosphonium, tetraphenylphosphonium and bis-(triphenylphosphine)iminium.

7. The process as defined by claims 2 or 6, wherein the anion of said quaternary onium salt is one of the following anions: $H_2PO_4^-$, $F^-$, $ClO_4^-$, $PF_6^-$, $BF_4^- B\Phi_4^-$, $PO_4^{3-}$, $HPO_4^{2-}$, $CH_3SO_3^-$,

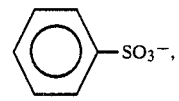

$HSO_4^-$, $NO_3^-$, $SO_4^{2-} Cl^-$, $Br^-$, $I^-$, $SCN^-$, $CN^-$ and $RS^-$, in which R represents a $C_1$-$C_6$ alkyl or $C_6$-$C_{10}$ aryl radical.

8. The process as defined by claim 7, wherein said anion is one of the following anions: $PO_4^3 - HPO_4^{2-}$, $H_2PO_4^-$, $CH_3SO_3^-$,

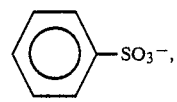

$NO_3^-$, $SO_4^{2-}$, $PF_6^-$, $Cl^-$ and $Br^-$.

9. The process as defined by claim 8, wherein said anion is a $Cl^-$ anion.

10. The process as defined by claims 1 or 2, wherein said polar alcohol is a monoalcohol having from 1 to 4 carbon atoms.

11. The process as defined by claim 10, wherein said polar alcohol is a monoalcohol having from 1 to 3 carbon atoms.

12. The process as defined by claim 10, wherein said apolar solvent has a dielectric constant of less than 2.3.

13. The process as defined by claim 12, wherein said apolar solvent has a dielectric constant of less than 2.1.

14. The process as defined by claim 13, wherein said apolar solvent is one of the following solvents: pentane, isopentane, hexane, cyclohexane, octane, cyclooctane, 2,2,4-trimethylpentane, decane, dodecane, tetradecane, hexadecane or admixtures thereof of petroleum ether type.

15. The process as defined by claim 12, wherein said contacting step (i) is carried out in the presence of:

(1) an amount of quaternary onium salt corresponding to a molar ratio quaternary onium cation/palladium of at least 20; and (2) amounts of alcohol and apolar hydrocarbon solvent which are at least equal to those required for the decantation of the contacting medium to provide an alcohol phase and an organic phase.

16. The process as defined by claim 15, wherein said contacting step (i) is carried out in the presence of:

(1) an amount of alcohol corresponding to a weight ratio quaternary onium salt/alcohol of at least 0.1; and (2) an amount of solvent corresponding to a weight ratio solvent/alcohol of more than 1.

17. The process as defined by claim 15, wherein said contacting step (i) is carried out in the presence of:

(1) an amount of quaternary onium salt corresponding to a molar ratio onium cation/palladium ranging from 20 to 200;

(2) an amount of alcohol corresponding to a weight ratio quaternary onium salt/alcohol ranging from 0.25 to 30; and (3) an amount of solvent corresponding to a weight ratio solvent/alcohol of more than 1.5.

18. The process as defined by claim 1, wherein the carbonylation reaction medium, which may contain unconverted alcohol, is treated with the quaternary onium salt, the apolar hydrocarbon solvent and, if necessary, the alcohol, the amounts of solvent and alcohol being adjusted such as to result in a separation of the alcohol phase and the organic phase after decantation; and recovering the alcohol phase containing the alcohol, the quaternary onium salt and the palladium catalyst.

19. The process as defined by claim 1, wherein the anion of said quaternary onium salt is a hard or intermediate base; the said quaternary onium salt is employed in whole or in part during the carbonylation reaction; the carbonylation reaction medium, which contains the onium salt and may contain unreacted alcohol, is treated with the onium salt the apolar hydrocarbon solvent and, the alcohol, the amounts of solvent and alcohol being adjusted such as to result in separation of the alcohol phase and the organic phase after decantation; and recovering the alcohol phase containing the alcohol, the quaternary onium salt and the palladium catalyst.

20. The process as defined by claim 19, wherein the amount of quaternary onium salt utilized for the carbonylation reaction corresponds to a molar ratio onium cation/palladium of more than 0.5.

21. The process as defined by claim 20, wherein the amount of quaternary onium salt utilized for the carbonylation reaction corresponds to a molar ratio onium cation/Pd ranging from 1 to 15.

22. The process as defined by any of claims 18 to 21, wherein the apolar solvent is introduced in whole or in part during the carbonylation reaction.

23. The process as defined by any of claims 1 and 18 to 22, further comprising extracting/separating the alcohol phase obtained upon decantation at least once with the said apolar hydrocarbon solvent.

* * * * *